United States Patent [19]
Fischer et al.

[11] Patent Number: 6,042,378
[45] Date of Patent: Mar. 28, 2000

[54] CONTAMINANT RETENTION RESISTANT TOOL

[75] Inventors: Dan E. Fischer; Dan J. Bills, both of Sandy, Utah

[73] Assignee: Ultradent Products, Inc., South Jordan, Utah

[21] Appl. No.: 08/807,564

[22] Filed: Feb. 19, 1997

[51] Int. Cl.$^7$ .................................................. A61C 3/00
[52] U.S. Cl. ............................................................. 433/141
[58] Field of Search .................................... 433/114, 141, 433/142, 143, 144, 145, 146, 147

[56] References Cited

U.S. PATENT DOCUMENTS

| | | | |
|---|---|---|---|
| 237,062 | 1/1881 | Starr | 433/147 |
| 1,039,235 | 9/1912 | Wiggins | 433/143 |
| 5,007,831 | 4/1991 | Bierbaum et al. | 433/114 |
| 5,478,235 | 12/1995 | Schuldt et al. | 433/37 |

*Primary Examiner*—Cary E. O'Connor
*Attorney, Agent, or Firm*—Workman, Nydegger, Seeley

[57] ABSTRACT

A dental or medical instrument has a body configured to be hand-held by a practitioner and a tip extending from the body. The body has a randomly textured gripping surface. The gripping surface is sufficiently textured to prevent a practitioner's fingers from slipping during use of the instrument, yet has minimal microbial contaminant retention. The coupling of the tip to the body defines a substantially seamless coupling interface.

13 Claims, 11 Drawing Sheets

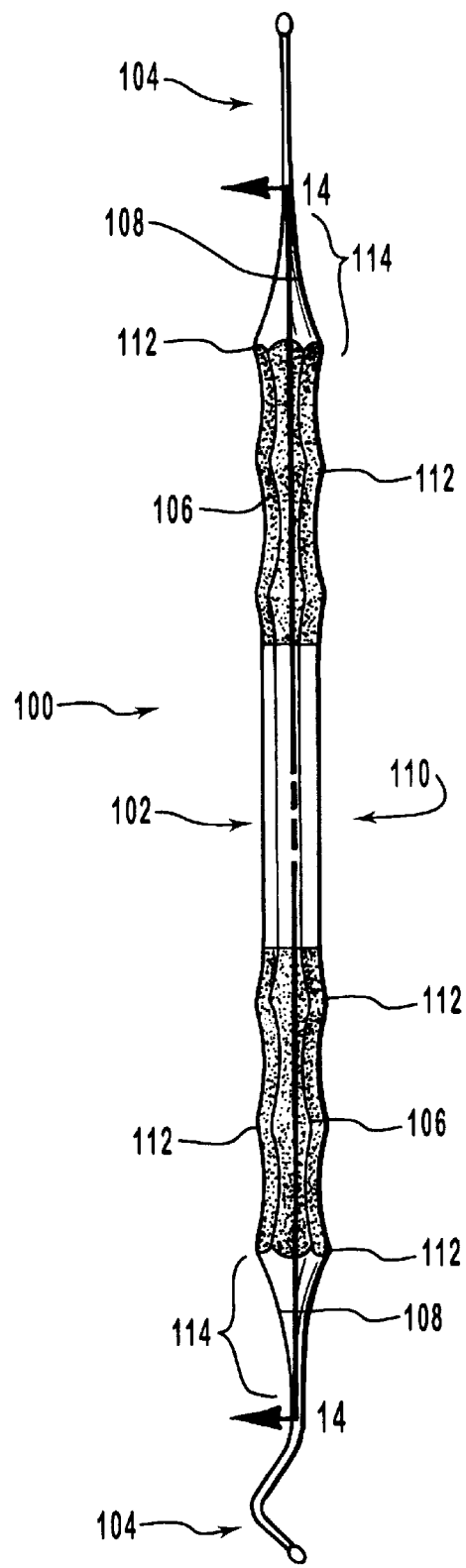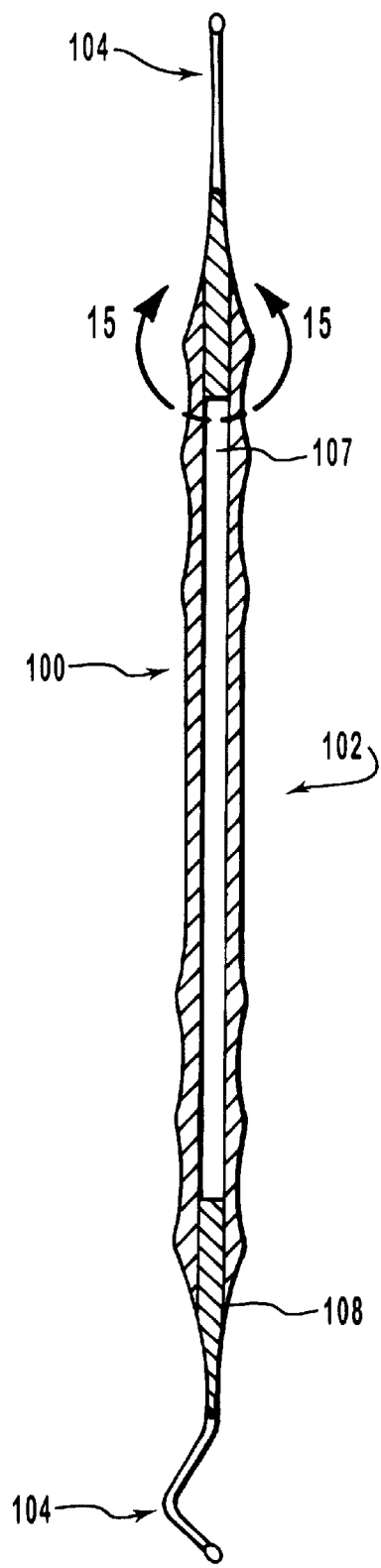
FIG. 13
FIG. 14

CONTAMINANT RETENTION RESISTANT TOOL

BACKGROUND

1. Field of the Invention

This invention is in the field of hand-held tools. More specifically, this invention relates to hand-held tools utilized primarily in medical and dental applications which have textured gripping surfaces and a tip extending from the body of the tool.

2. State of the Art

Since medical and dental instruments contact and are inserted within a patient's body, it is a vital to the health of a patient to treat the patient with sterile instruments. On the other hand, microorganisms infest the earth, colonizing in locations with a suitable temperature in which they can find a nutrient source. Nutrient sources which are entrapped within a partially-enclosed space on a tool, such as a medical or dental instrument, encourage microbial growth within the space, causing microorganisms to grow, reproduce and colonize. As a result, clumps of microorganisms form and remain entrapped within such spaces. Even when attempts are made to clean a tool having partially-enclosed spaces, the exterior microbes of the microbial mass often shield the interior microbes, thus hampering attempts to remove the microbial mass from a particular space.

Removal of microorganisms from spaces which are conducive to entrapment is a particular problem in the field of hand-held tools utilized in dental or medical applications. Such hand-held tools generally have textured surface areas to prevent a practitioner's hand from slipping during use of the tool. For example, the surface of a particular hand-held tool may be textured with knurls, ridges, grooves, or other machined surfaces to form a gripping surface which a practitioner grasps during use of the tool.

Unfortunately, however, the textured or roughened surface area also encourages microbial entrapment. Saliva, clotted blood, and other bodily fluids that are embedded in a groove or a space between knurls (an "interknurlular space") can become a nutrient source for microbes.

The knurls or ridges of typical machined gripping surfaces are high profile, or in other words, have high peak to valley ratios. Because of the high profile knurls, large interknurlular spaces exist. These machined, high profile surfaces encourage nutrient entrapment and subsequent microbial ingrowth within the interknurlular spaces.

In addition, certain hand-held tools include a rough transition between the tip of the tool and the body of the tool. For example, the insertion of a tip may create an annular ridge adjacent to the tip, thereby providing a ledge which entraps nutrients, promoting microbial ingrowth. Accordingly, the space between the annular ridge and the tip is highly susceptible to the colonization of microbes.

In addition, knurls, ridges or other raised surfaces are typically not distributed densely throughout the gripping surface, but instead, are spaced relatively far apart, leaving large gaps between the raised surfaces. Another difficulty with machined surfaces in general is that machined surfaces include raised surfaces which are typically raised a uniform distance above the body of the tool.

While it is possible to provide a smooth surface on a particular dental tool in order to avoid nutrient entrapment and subsequent promotion of microbial ingrowth, smooth surfaces are slippery, particularly when covered with fluid and held by a practitioner wearing a latex glove. Some have attempted to provide a non-slip smooth gripping surface by disposing a rubber grip about the tool. However, the interface between the rubber grip and the body of the tool provides an environment that is highly susceptible to microbial ingrowth. The interface retains water and microbial nutrients and is difficult, if not impossible, to decontaminate.

By way of example, FIG. 1 is a top view of a dental tool 10 of the prior art having a knurled gripping surface 12 and a rough, stepped transition 14 between a body 16 of tool 10 and a tip 18 coupled to tool 10. As shown in FIG. 1, the annular ridge 20 formed at the interface 14 between the tip 18 and the body 16 of tool 10 is a site which encourages nutrient entrapment and subsequent microbial ingrowth. FIG. 3 demonstrates a cross sectional view of tool 10 through knurled gripping surface 12. As shown in FIG. 3, the high profile knurls 24 have high peak to valley ratios, making the large interknurlular spaces 22 ideal for nutrient entrapment and subsequent microbial ingrowth. Both the annular ridge 20 and the interknurlular spaces 22 are difficult to clean and encourage growth of clumps of microorganisms which are difficult to eradicate. In addition, as shown, the distribution and the peak to valley ratio of the various machined knurls 24 is uniform. The distance between knurls 24 is also uniform.

Also by way of example, FIG. 2 is a top view of another dental tool 30 of the prior art having a ridged gripping surface 32 and a tip 34 integrally extending from a body 36. As shown in cross section in FIG. 4, the grooves 38 between the ridges 40 of tool 30 are also ideal for nutrient entrapment and subsequent microbial ingrowth and are difficult to clean.

FIGS. 5 and 6 demonstrate magnified views of rough transitions between bodies and tips of dental instruments of the prior art. As shown, a dramatic ridge exists for entrapment of nutrient sources and for subsequent microbial ingrowth.

FIGS. 7 and 8 demonstrate top and cross sectional magnified views, respectively, of a "knurled and parted" grip of the prior art. These figures demonstrate the high peak to valley ratios existing on a knurled surface and the entrapment which may occur in an interknurlular space or within the "parted" or channeled portion of the grip, shown in FIG. 7.

FIGS. 9 and 10 demonstrate top and cross sectional magnified views, respectively, of a cut groove grip employed in dental tools in the prior art. As shown, the exterior surface of the cut groove grip is generally smooth, but the cut groove provides a deep recess for nutrient entrapment and microbial ingrowth, thus featuring slipperiness on the non-grooved exterior surface and risking bacterial contamination in the groove.

FIGS. 11 and 12 demonstrate top and cross sectional views, respectively, of a stamped groove grip of a dental tool of the prior art featuring a smooth exterior surface which has been stamped to provide texture. As shown, the grooves provide a wide recess for the entrapment of microorganisms while the remainder of the exterior surface is smooth, thus featuring slipperiness on the non-stamped exterior surface and risking bacterial contamination in the recess.

BRIEF SUMMARY AND OBJECTS OF THE INVENTION

It is therefore an object of the invention to provide an improved hand-held tool.

It is a further object of the invention to provide a hand-held tool having minimal microbial contaminant retention.

It is a further object of the invention to provide a hand-held tool which is sufficiently textured to prevent a practitioner's fingers from slipping during use of the tool, while also yielding minimal microbial contaminant retention.

It is another object of the invention to provide a hand-held tool having a randomly textured gripping surface.

It is another object of the invention to provide a hand-held tool having a body and tip coupled to the body, defining a coupling interface, wherein the coupling interface is substantially seamless.

It is a further object of the invention to provide a method for manufacturing a handheld tool having minimal microbial contaminate retention.

It is a further object of the invention to provide a tool which is less likely to entrap microorganisms and their nutrient sources and facilitates the removal of microorganisms and their nutrient sources from the exterior surface of the tool.

The present invention relates to a tool comprising a gripping portion and ends on opposing sides of the gripping portion. At least one of the ends is configured for use in a medical or dental procedure.

In one embodiment, a body is configured to be hand-held by a practitioner and a tip extends from the body. Preferably, the body has a randomly textured gripping surface, such as a gritblasted gripping surface. The randomly textured gripping surface provides texture for gripping, yet lacks deep pits and interknurlular spaces in which nutrients and microbes become entrapped. The randomly textured surface is low profile or, in other words, features low peak to valley ratios. Thus, the surface does not retain nutrient sources as readily, for example, as a typical knurled surface.

The randomly textured surface is also densely textured, rather than having texturing spread apart as with knurls, or typical grooves and cut surfaces. The randomly textured surface also features varied peak height, avoiding the slippery dynamic caused by uniform peaks. Because of its random texturing, the surface is sufficiently textured to prevent a practitioner's fingers from slipping during use of the tool, yet promotes minimal microbial contaminant retention.

In another embodiment, the tip is coupled to the body in such a manner as to define a substantially seamless coupling interface between the tip and the body. This smooth interface minimizes entrapment of microbial nutrients which could otherwise accumulate at the interface between the tip and the body.

In the foregoing embodiments, sterilization through a chemical process or through autoclaving, for example, kills bacteria on the hand-held tool because the bacteria is not sequestered in thick clumped groups. Furthermore, microorganisms and their nutrient sources are more readily removed from the exterior surface of the tool.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings as hereinafter described.

FIG. 13 is a top view of a hand-held tool of the present invention.

FIG. 14 is a cross sectional view of the hand-held tool of the present invention demonstrated in FIG. 13 taken along lines 14—14.

DETAILED DESCRIPTION OF THE PREFERRED EMBODIMENTS

Figure 1:
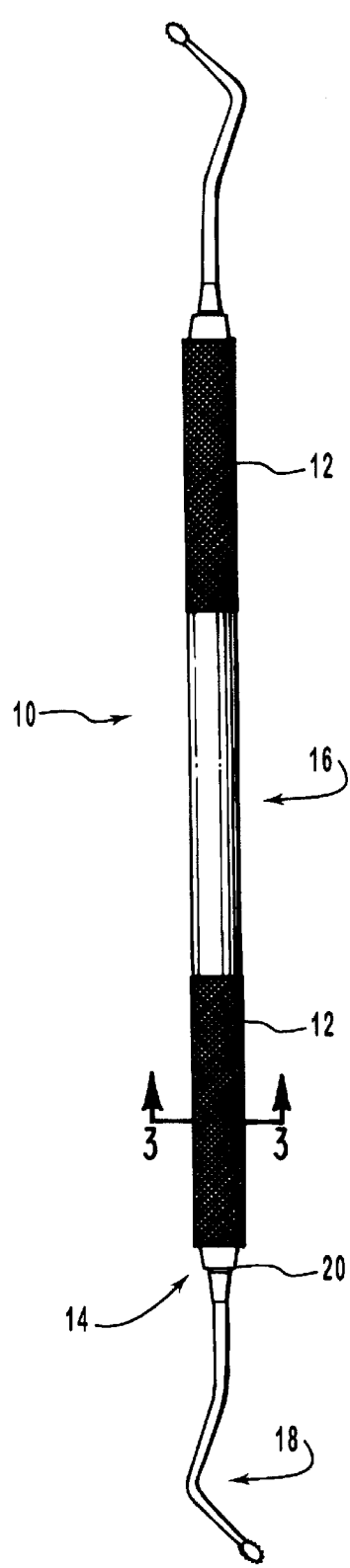
FIG. 1 is a top view of a dental tool of the prior art having a uniformly knurled gripping surface and a rough, stepped transition between a body of the tool and a tip coupled to the tool.
Figure 2:
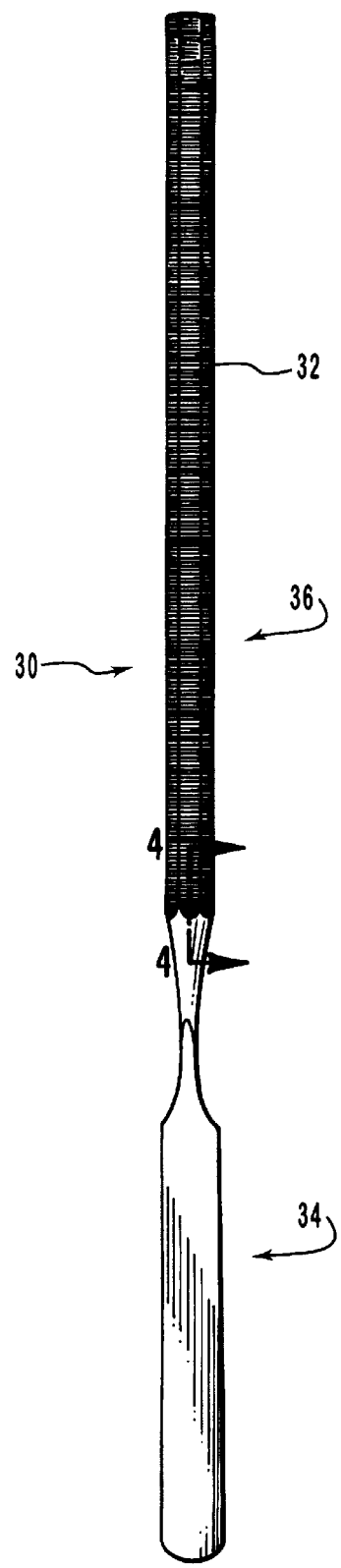
FIG. 2 is a top view of another dental tool of the prior art having a uniformly ridged gripping surface and a tip extending integrally from a body.
Figure 3:
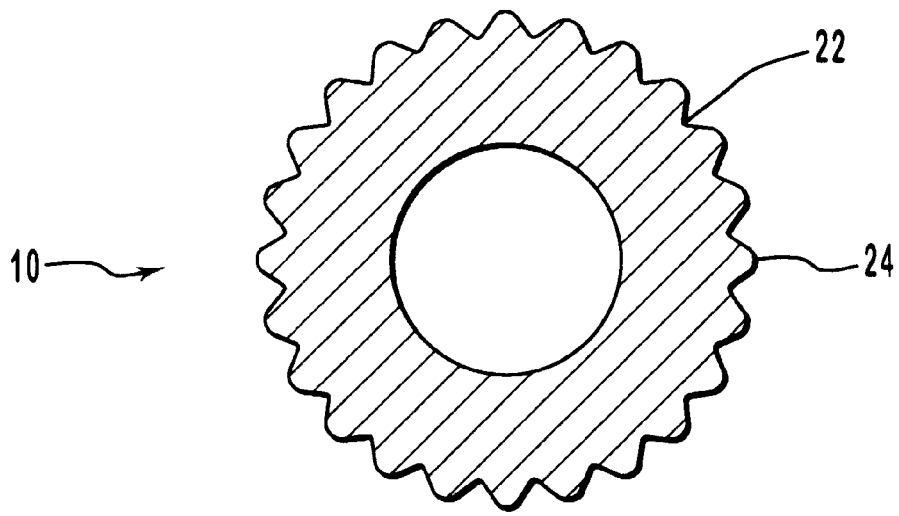
FIG. 3 demonstrates a cross sectional view of the tool of FIG. 1 taken along lines 3—3.
Figure 4:
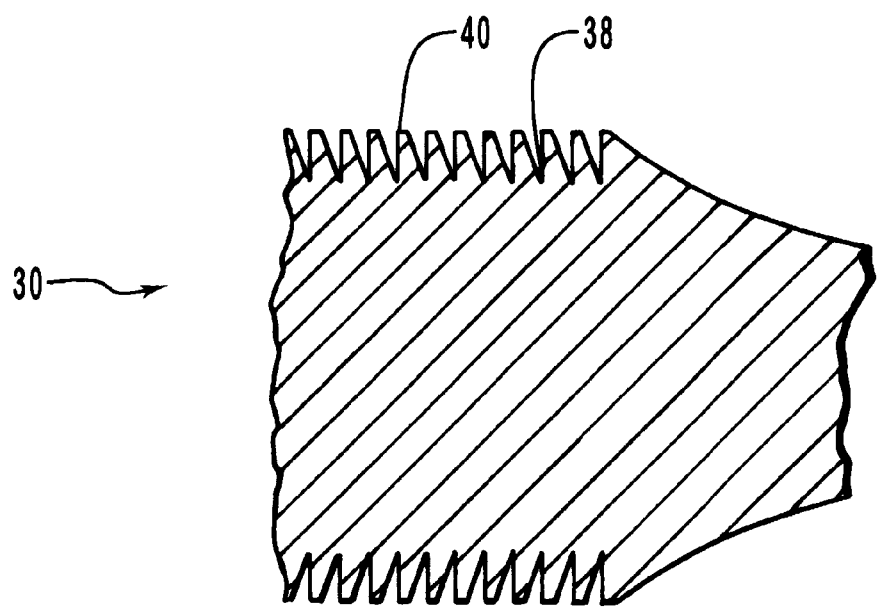
FIG. 4 demonstrates a cross sectional view of the tool of FIG. 2 taken along lines 4—4.
Figure 5:
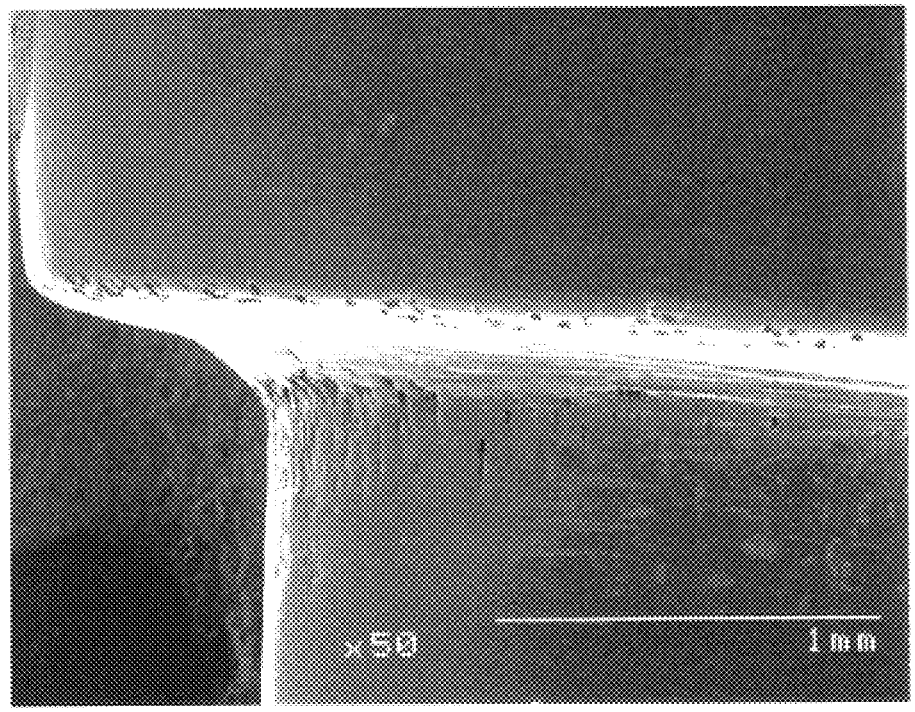
FIG. 5 is a picture taken from a top view of an interface between an integral tip and a body of a tool of the prior art as magnified at 50× under a scanning electron microscope.
Figure 6:
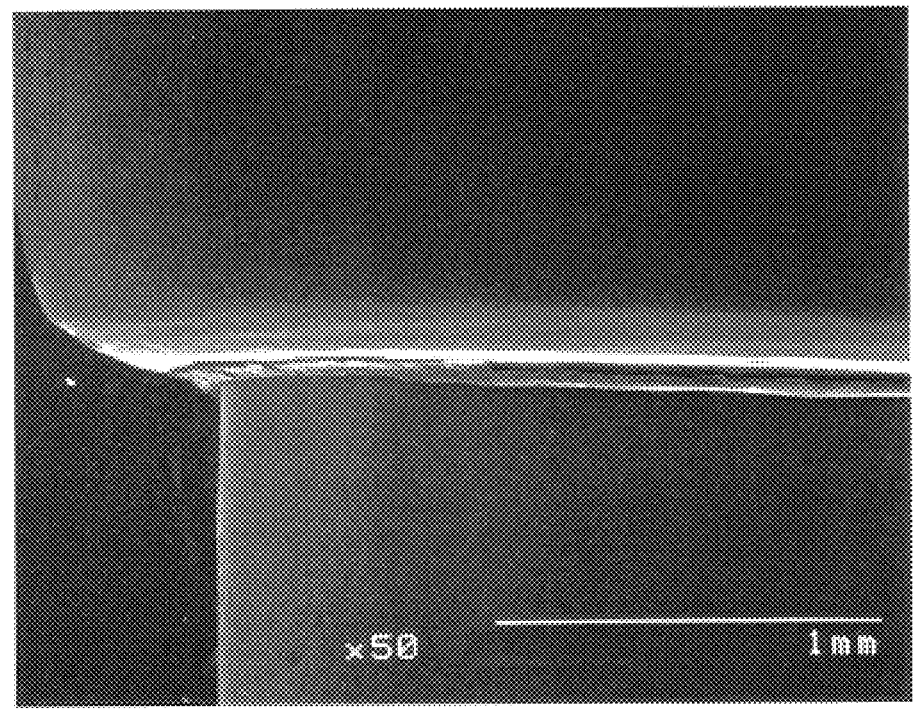
FIG. 6 is a picture taken from a top view of an interface between a coupled tip and a body of a tool of the prior art as magnified at 50× under a scanning electron microscope.
Figure 7:
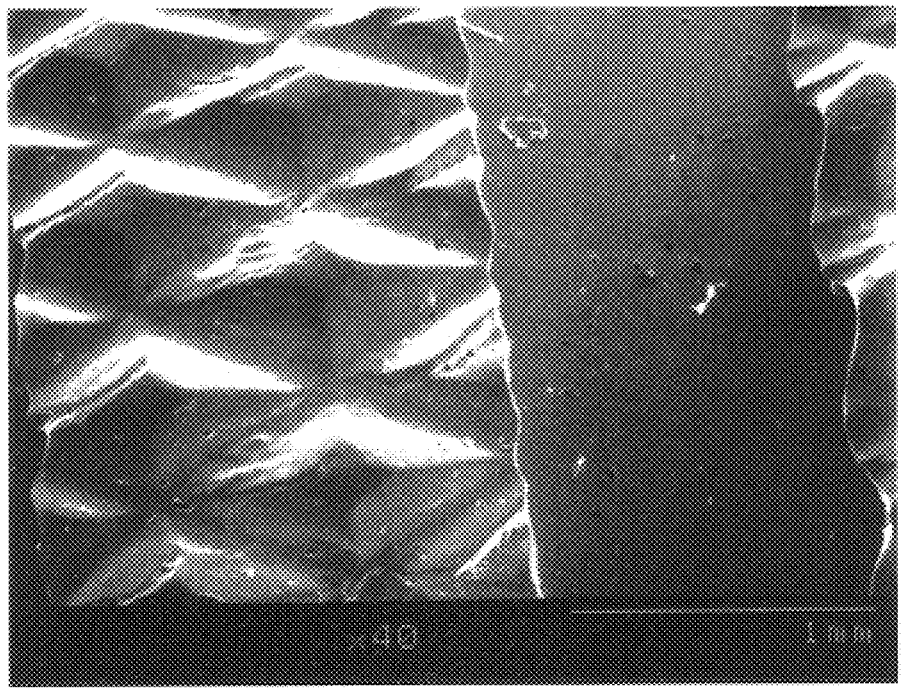
FIG. 7 is a picture taken from a top view of a tool of the prior art having a "knurled and parted" grip, as magnified at 40× under a scanning electron microscope. The parted portion consists of a channel between the knurled portions shown.
Figure 8:
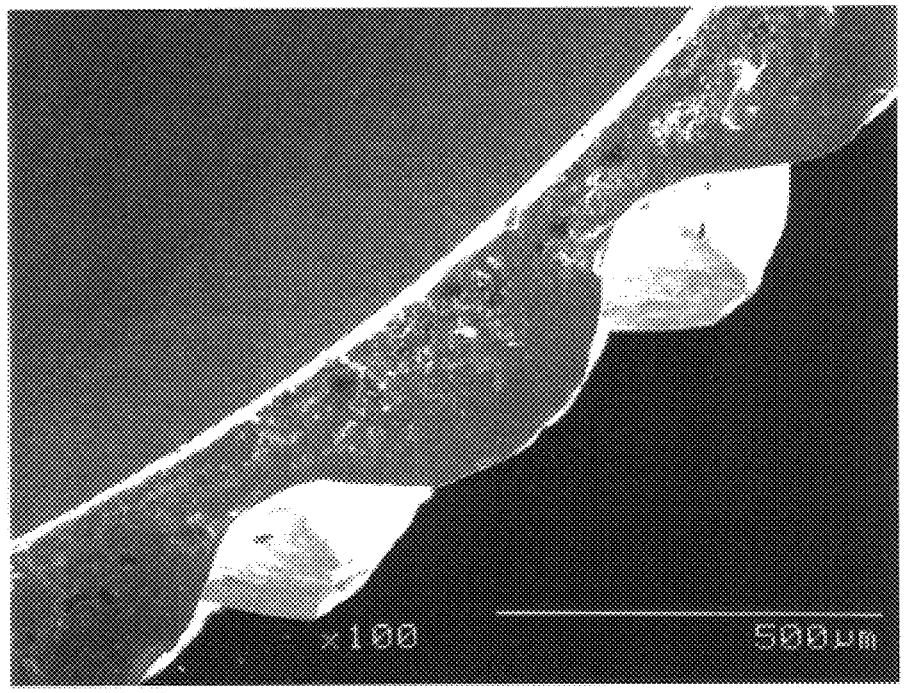
FIG. 8 is a picture taken from a cross sectional view of the tool shown in FIG. 7, as magnified at 100× under a scanning electron microscope, demonstrating the high profile peaks and valleys of the knurls of the gripping surface.
Figure 9:
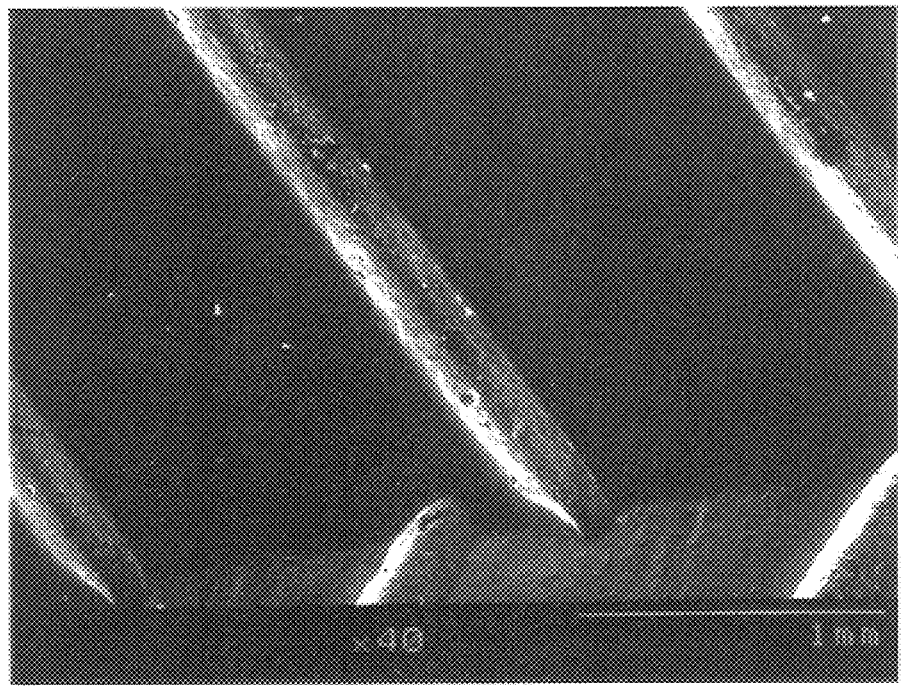
FIG. 9 is a picture taken from a top view of a tool of the prior art having a cut groove grip, as magnified at 40× under a scanning electron microscope.
Figure 10:
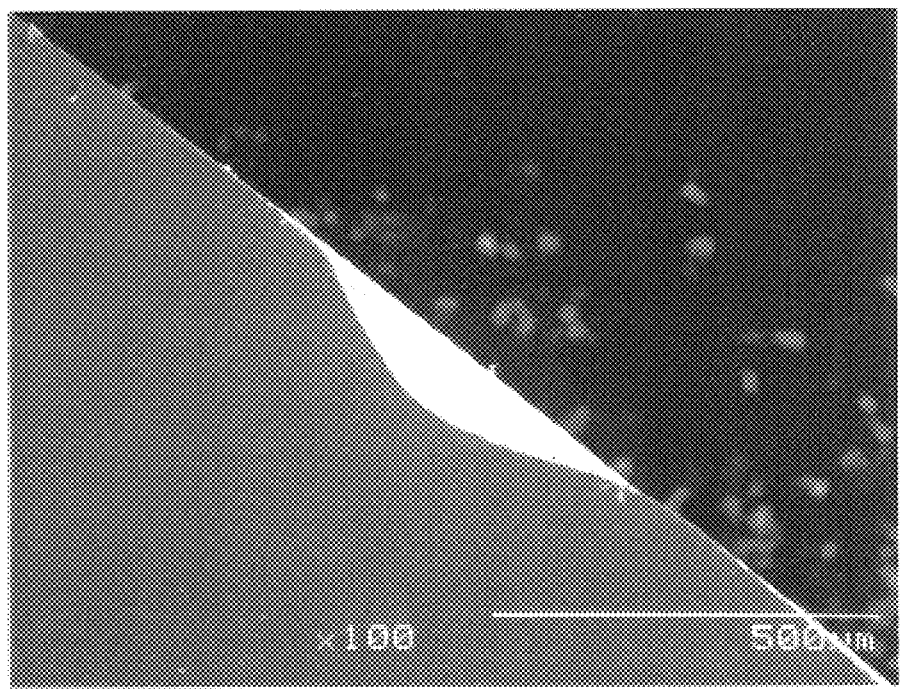
FIG. 10 is a picture taken from a cross sectional view of the tool shown in FIG. 9, as magnified at 100× under a scanning electron microscope, demonstrating the smooth exterior, non-cut portion and the deep valley of the cut portion.
Figure 11:
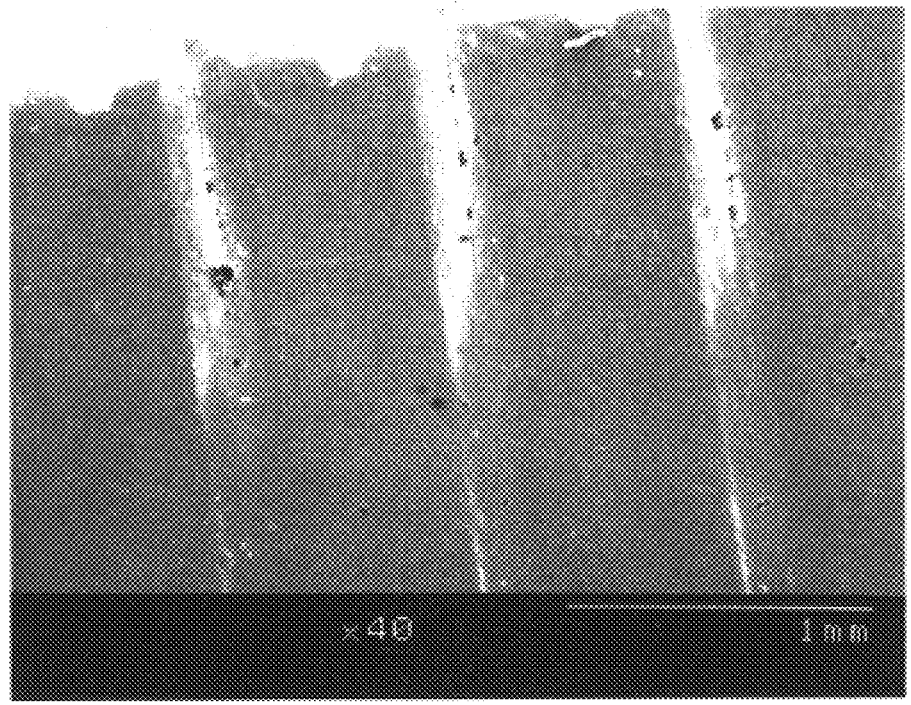
FIG. 11 is a picture taken from a top view of a tool of the prior art having a stamped groove grip, as magnified at 40× under a scanning electron microscope.
Figure 12:
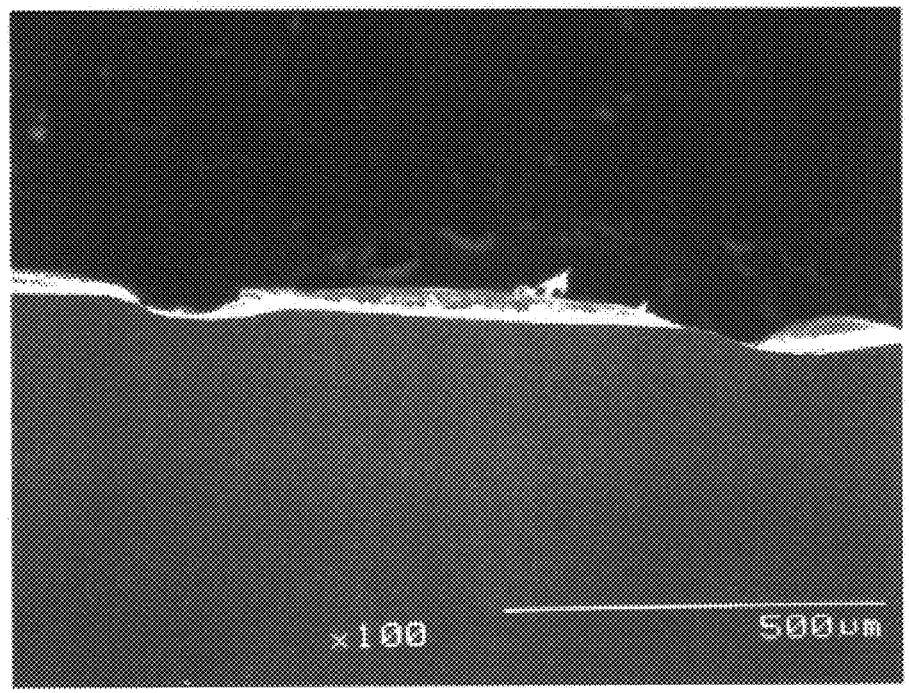
FIG. 12 is a picture taken from a cross sectional view of the tool shown in FIG. 11, as magnified at 100× under a scanning electron microscope, demonstrating the smooth exterior, non-stamped portion and the wide recess of the stamped portion.
Figure 15:
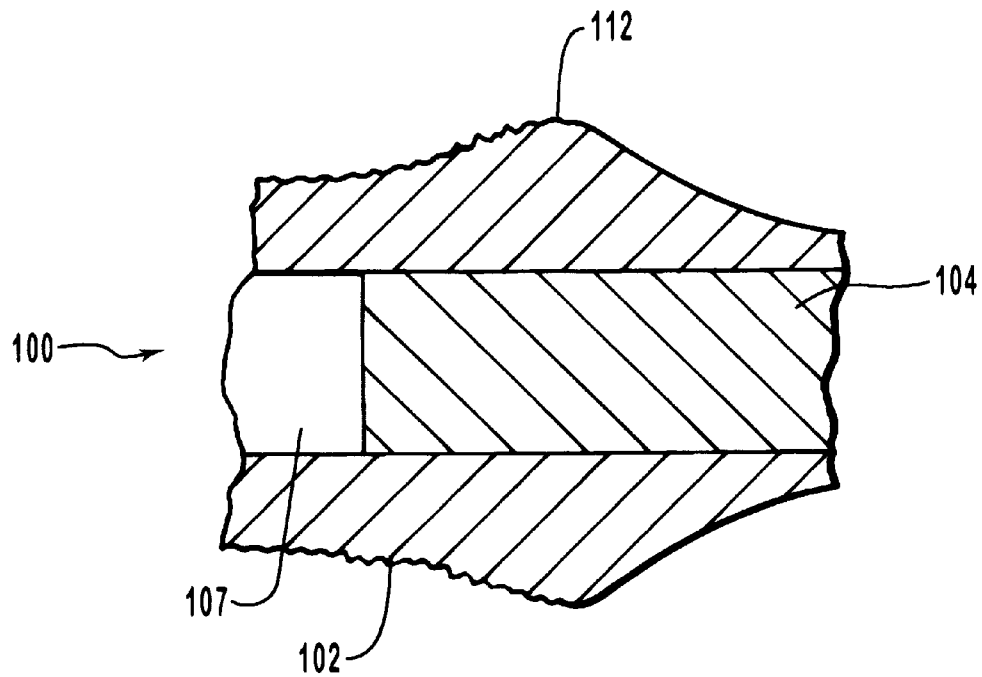
FIG. 15 is an enlarged cutaway view of the hand-held tool of the present invention demonstrated in FIG. 13 taken along lines 15—15 of FIG. 14, demonstrating an exterior convolution available in one embodiment of the present invention.

With reference now to FIGS. 13–15, in one embodiment, the present invention relates to a hand-held tool 100 comprising a body 102 and at least one tip 104 extending from body 102, such as by being coupled to body 102 or extending integrally from body 102. Body 102 is configured to be hand-held by a practitioner. At least one gripping surface 106 on body 102 aids in preventing a practitioner's fingers from slipping from body 102 during use of tool 100.

In one embodiment, body 102 includes randomly textured gripping surfaces 106 on opposing sides of body 102, such as gritblasted, chemically etched, or electrically treated gripping surfaces. Because of their random texturing, gripping surfaces 106 are sufficiently textured to prevent a practitioner's fingers from slipping during use of tool 100, yet, as opposed to machined surfaces, promote minimal microbial contaminant retention.

In another embodiment, each tip 104 is coupled to body 102 in such a manner as to define a substantially seamless coupling interface 108 between the tip 104 and body 102. This smooth interface 108 minimizes entrapment of microbial nutrients which could otherwise accumulate at an interface between a tip and a body of a hand-held tool.

Because of these and other features, microorganisms and their nutrient sources are more readily cleaned from tool 100. As used throughout this specification and the appended claims, the terms "clean" or "cleaned" refer to any process of cleansing tool 100, such as through washing, sterilization, heating, autoclaving, wiping, and a variety of physical, mechanical, and chemical cleansing processes.

Hand-held tool 10 can be employed in a variety of industries and is particularly useful in the fields of medicine and dentistry such as maxillofacial surgery and various dental applications. Body 102, gripping surfaces 106, tips 104, and other features of the invention will now be discussed in additional detail below.

Figure 16:
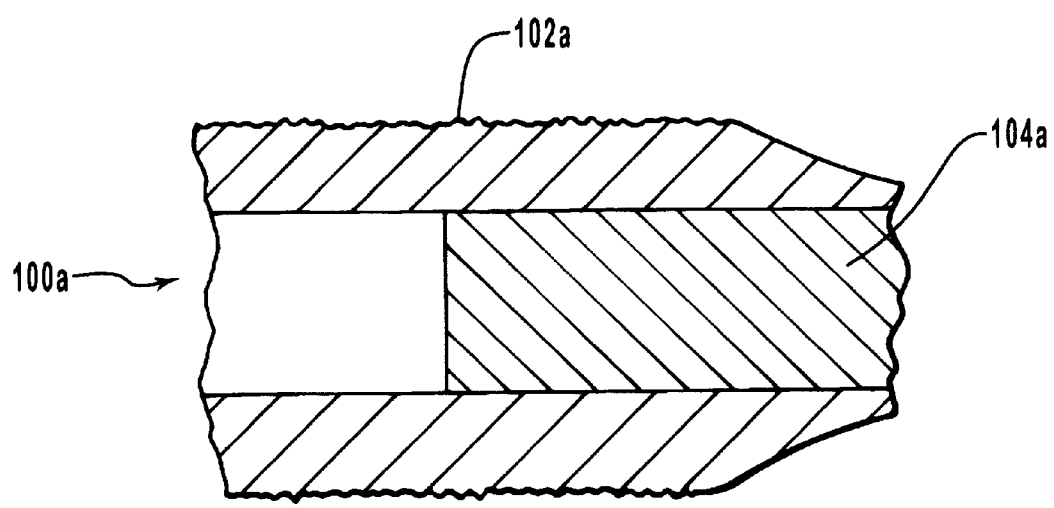
FIG. 16 is a cutaway view of an alternative hand-held tool of the present invention without the convolution on the exterior surface shown in FIG. 15.
Figure 17:
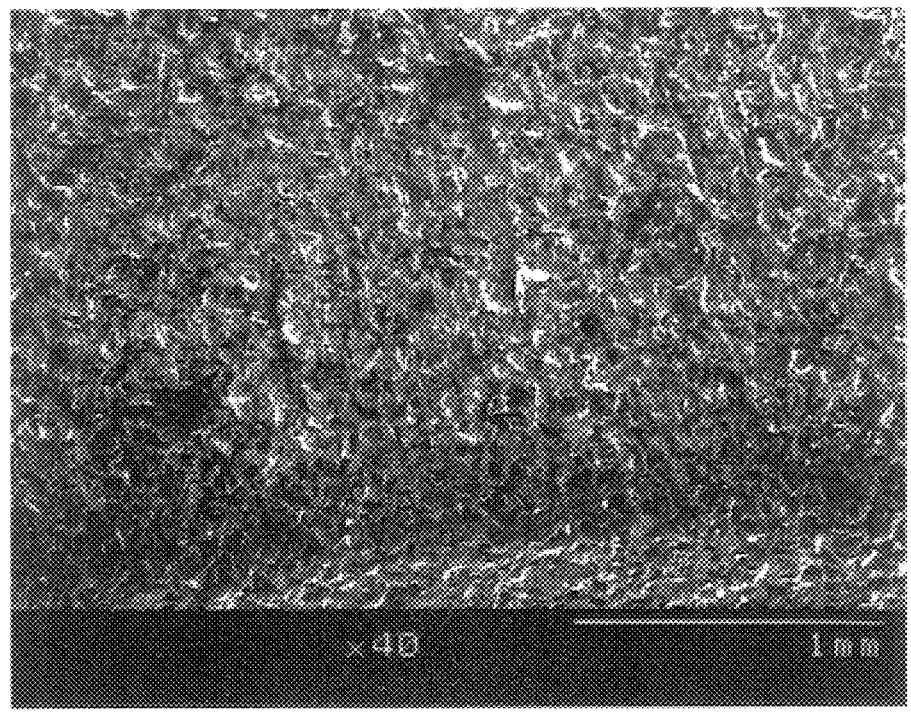
FIG. 17 is a picture taken from a top view of the sandblasted gripping surface of a tool of the present invention, as magnified at 40× under a scanning electron microscope, demonstrating the densely textured sandblasted surface.
Figure 18:
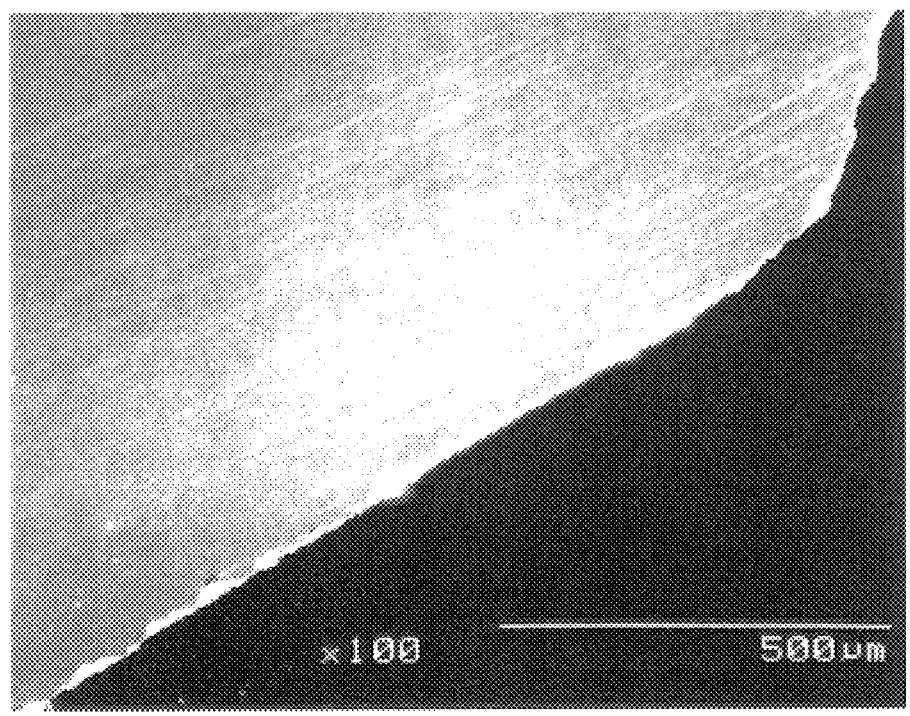
FIG. 18 is a picture taken from a cross sectional view of the tool of the present invention shown in FIG. 17, as magnified at 100× under a scanning electron microscope, demonstrating the varied, small profile, peak to valley ratios of the sandblasted surface.

Although a variety of configurations may be used for body 102, body 102 is preferably comprised of an elongate member 110, as shown in FIG. 13. In order to reduce the weight of body 102, body 102 is preferably hollow, defining a chamber 107, as shown in FIGS. 14 and 15. In one embodiment, in order to improve a practitioner's grip on body 102, body 102 includes convolutions 112, such as the series of three peaks and corresponding valleys shown in FIGS. 13 and 14 on each of the opposing sides of body 102. However, the invention may also include a non-convoluted surface, as shown in the body 102a of tool 100a in FIG. 16. In addition, the preferred cross section transverse to the longitudinal axis of body 102 is configured in the shape of an octagon (with the exception of the smooth, rounded, tapering neck region 114, discussed below) thereby allowing the practitioner to grip various flattened surfaces, as opposed to rounded surfaces.

The random texturing processes of the present invention sufficiently roughen gripping surfaces 106 of body 102 to prevent slipping, but create surfaces which are sufficiently low profile (low peak to valley ratio) in nature to minimize microbial retention. Thus, microorganisms and their nutrient sources are more readily cleaned from the randomly textured gripping surfaces 106.

As used throughout this specification and the appended claims, a "randomly textured" gripping surface comprises a gripping surface in which the texturing is achieved through a texturing method which textures the surface without a predetermined design for the specific shape and contours of the surface. Examples of a random texturing method include gritblasting, such as sandblasting or gritblasting with another abrasive medium, chemical etching, and electrical treating.

Mechanical texturing, on the other hand, does not produce a randomly textured surface, but instead is carried out by a practitioner who designs the texture in advance, then produces a knurled, cut, knurled & parted, stamped, or other textured surface achieved through the use of a lathe or machine. Typically, a machined surface includes a direction and a predetermined pattern which is generally uniform or symmetrical. Peaks and grooves have a predetermined direction and contour, as shown in FIGS. 1–12. Mechanical texturing is also typically not densely distributed. A random texture also excludes an elastomeric grip which includes a predetermined, molded design.

With reference to FIGS. 13–20, a randomly textured surface features texturing which is irregularly (non-uniformly) and densely distributed throughout the entire surface of the gripping area. The surface also includes peaks and valleys which vary in size and shape and are low profile relative to typical machined surfaces, such as knurled or pressed surfaces.

As shown in FIGS. 13–18, for example, sand-blasting or another type of gritblasting creates a low profile texture which is not predetermined, and which is densely and irregularly dispersed, more finely texturing the surface area to be gripped by the practitioner. As shown, the low profile sandblasted surface provides texture for gripping, yet lacks deep pits and interknurlular spaces in which nutrients and microbes become entrapped. Thus, the sandblasted gripping surface does not retain nutrient sources as readily, for example, as a knurled surface. In addition, the peak heights and shapes are irregularly varied, rather than uniform, thereby avoiding the slippery dynamic caused by uniformly raised peaks. In one embodiment, the peak to valley ratio of the randomly textured gripping surface, such as the sandblasted gripping surface, is in the range of about 1 to about 50 microns.

Figure 19:
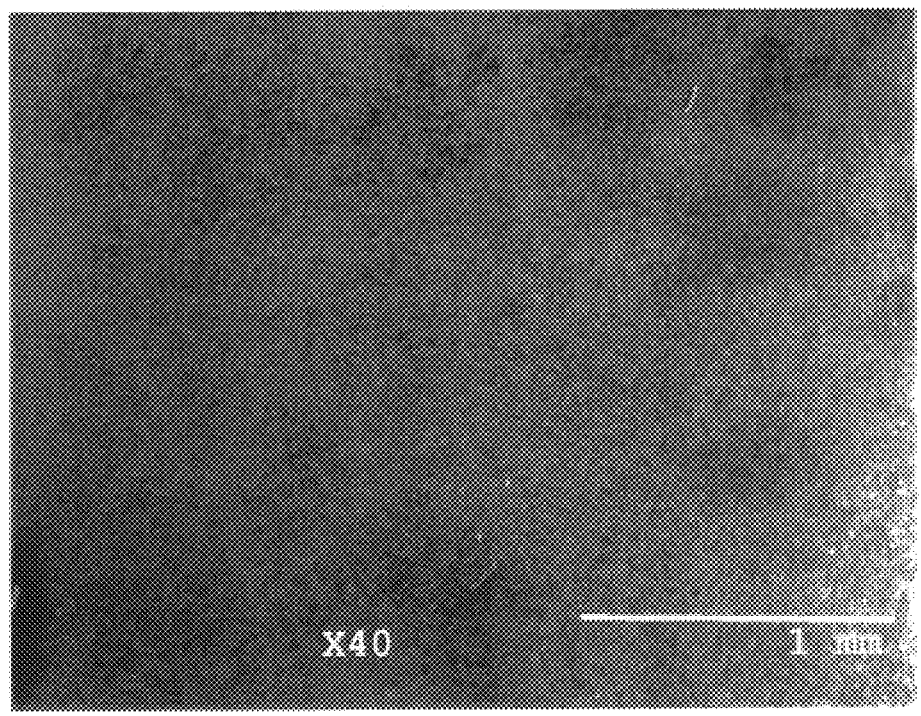
FIG. 19 is a picture taken from a top view of a tool of the present invention having an acid-etched gripping surface, as magnified at 40× under a scanning electron microscope.
Figure 20:
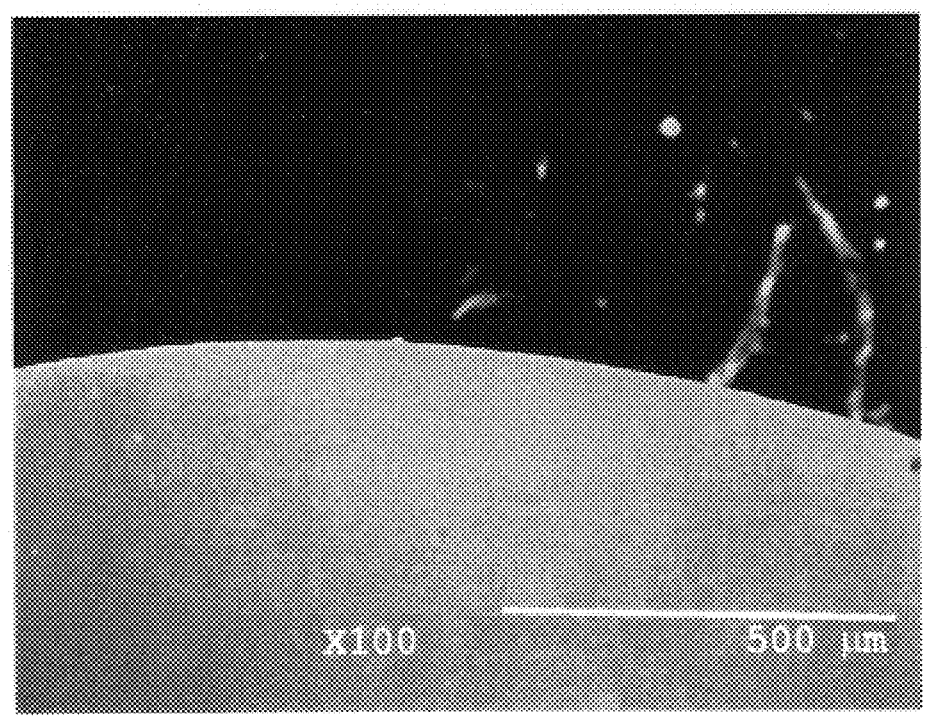
FIG. 20 is a picture taken from a cross sectional view of the tool of the present invention shown in FIG. 19, as magnified at 100× under a scanning electron microscope, demonstrating the small profile peak to valley ratios of the acid-etched exterior surface.
Figure 21:
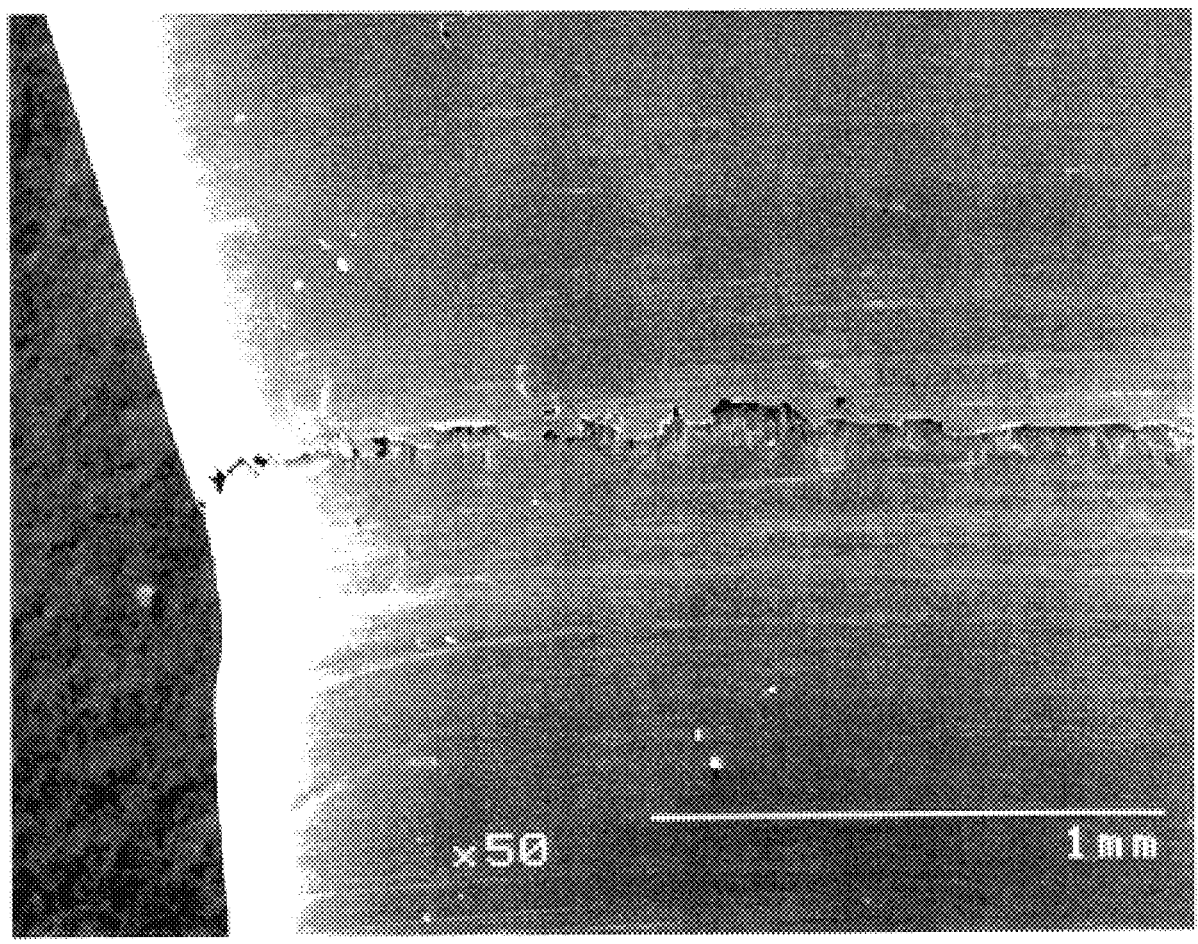
FIG. 21 is a picture taken from a top view of a tool of the present invention, as magnified at 50× under a scanning electron microscope, demonstrating a smooth, substantially seamless interface between a tip and a body of the tool.

Examples of a chemical etching process include acid etching, alkaline etching, or other chemical processes which etch the exterior of a body of a tool. An example of an acid-etched gripping surface is shown in FIGS. 19 and 20. Electrical treatments such as electrolytic etching, electrocoating or other electrical processes also serve as examples of random texturing processes.

In one embodiment, because of the unique texturing of the randomly textured gripping surface 106, the texture of the gripping surface is configured such that microorganisms are not present on the gripping surface 106 in a concentration that is substantially greater than the concentration of microorganisms on a non-textured portion of body 102 after the tool has been used in a dental or medical procedure and is subsequently cleaned. For purposes of this specification and the appended claims, the phrase "substantially greater than the concentration of microorganisms on a non-textured portion of the body" or a similar phrase refers to a concentration of microorganisms that is: (i) less than one order of magnitude greater than the concentration of microorganisms on the non-textured portion of the body 102; (ii) preferably no more than about 400 percent greater than the concentration of microorganisms on the non-textured portion of the body 102; (iii) more preferably no more than about 200 percent greater than the concentration of microorganisms on the non-textured portion of the body 102; or (iv) most preferably no more than about 150 percent greater than the concentration of microorganisms on the non-textured portion of the body 102.

The textured surface thus provides sufficient friction for gripping with a roughness which minimizes entrapment of nutrients and subsequent ingrowth of microorganisms. As a result, tool 100 is more readily cleaned and sterilization kills bacteria on the randomly textured surface because the bacteria is not sequestered in thick clumped groups.

While in one embodiment body 102 of tool 100 is integral with the tip 104, in a preferred embodiment, tip 104 is coupled to body 102 after body 102 has been substantially formed. As used in this specification and the appended claims, the term "coupled" refers to a tip which is separate from the body and which is anchored to the body, rather than being integrally formed with the body. The terms "couple" or "coupling" refer to a process of anchoring a tip which is separate from a body to the body.

The advantage of coupling a tip 104 to a body 102 is that it allows the practitioner to purchase or otherwise provide a number of bodies into which the practitioner may place a variety of different tips. The tips and bodies may be manufactured separately, then coupled. Coupling the tips to the body is often less cumbersome and less expensive than manufacturing a body with an integral tip.

In addition, different materials can be readily used for the tip and the body when the tip is not integrally formed. For example, in one embodiment, tips 104 comprise 410 stainless steel (410 SS) while body 102 comprises 304 stainless steel (304 SS).

As shown in FIGS. 14 and 15, in the present invention, the opposing ends of body 102 are configured to receive separate tips 104. Body 102 is configured to receive a tip 104 such as by providing a hollow tubular chamber 107 in which tip 104 is anchored. In another embodiment, only one tip 104 is coupled to body 102. In another embodiment, the tip is coupled to the body by being anchored around body 102.

In order to prevent nutrient entrapment and subsequent microbial ingrowth, it is preferred in the present invention to provide a smooth interface 108 between body 102 and tip 104. As opposed to the prior art, however, tips 104 are coupled to body 102 in such a manner as to define a substantially seamless coupling interface 108 between tips 104 and body 102.

It will be appreciated that the term "substantially seamless coupling interface" or a similar term as used throughout this specification and claims relates to: (i) an interface having a gap between the exterior surface of body 102 and the exterior surface of tip 104 which is no greater than about 0.1 mm, preferably no greater than about 0.025 mm, more preferably no greater than about 1 micron or less; (ii) an interface on which the human hand cannot feel any distinction between tip 104 and body 102 as one rubs a hand over the interface; (iii) an interface having a distinction between tip 104 and body 102 which is unobservable with the naked eye; (iv) an interface which is configured such that the concentration of microorganisms at the interface is not substantially greater than the concentration of microorganisms on tip 104 or a nontextured portion of body 102 after the tool has been used in a dental or medical procedure and is subsequently cleaned; or (v) an interface which is welded to partially or totally eliminate a gap between body 102 and tip 104.

As used throughout this specification and the appended claims the phrase "substantially greater than the concentration of microorganisms on tip 104 or a nontextured portion of body 102" or a similar phrase refers to a microbial concentration at interface 108 which is: (i) less than one order of magnitude greater than the concentration of microorganisms on tip 104 or a non-textured portion of the body 102; (ii) preferably no more than about 400 percent greater than the concentration of microorganisms on tip 104 or a non-textured portion of the body 102; (iii) more preferably no more than about 200 percent greater than the concentration of microorganisms on tip 104 or a non-textured portion of the body 102; or (iv) most preferably no more than about 150 percent greater than the concentration of microorganisms on tip 104 or a non-textured portion of the body 102.

Various tips may extend from body 102. As used throughout this specification and the appended claims, the term "tip" refers to any object, device, or member which extends from body 102. In one embodiment, tip 104 comprises an excavator, as shown in FIGS. 13 and 14. In another embodiment, tip 104 comprises an explorer. Other embodiments of tip 104 include an interproximal carver, a composite packer, an enamel hatchet, a mirror, and a variety of other tips employed in the field of dentistry or medicine and in other fields for manipulating objects, cutting surfaces, scraping, scratching, adjusting, manipulating and other procedures. Tips 104 may be coupled to body 102 in a variety of manners including a friction fit, as shown in FIGS. 13–15 and 21, threaded, welded, or attached with an adhesive In one embodiment, body 102 is thicker than tips 104, allowing a practitioner to grip body 102 and dispose a distal end of tip 104 within a small area, such as within a crevice in a patient's tooth. In order to provide a substantially seamless coupling interface 108 between body 102 and thinner tips 104, as shown in FIGS. 13 and 14, in one embodiment, the present invention features a neck region 114 which tapers smoothly from the thicker portion of body 102 to tip 104. Despite the originally separate nature of body 102 and tip 104, this smooth neck 114 is accomplished by polishing neck 114 according to methods known by those skilled in the art. The polishing also yields a substantially seamless coupling interface 108 located at neck region 114.

In one embodiment, neck 114 is integral with body 102. In another embodiment, neck 114 is integral with tip 104. In yet another embodiment, as shown in FIGS. 13–15 and 21 body 102 and tip 104 each include a tapering portion which is configured to correspond, forming a single smooth neck 114. As shown in FIGS. 13 and 14, in a preferred embodiment, tool 100 includes a tip 104 and a corresponding neck 114 on each side of body 102.

The substantially seamless interface 108 prevents microbial ingrowth in the transition between body 102 and tip 104.

As a result, tool 100 is more readily cleaned and sterilization kills bacteria on the interface 108 because the bacteria is not sequestered in thick clumped groups.

It will be appreciated that a variety of methods exist for preparing or manufacturing a hand-held tool 100 of the present invention. One embodiment includes cutting a tube to the proper length desired for body 102, machining convolutions 112, and shaping the cross section of the outer surface of the body 102 into an octagon. Tips 104 are coupled to the outer ends of body 102 such as by anchoring tips 104 to body 102 with a friction fit. Mirrors or other tips may be anchored via threads, for example, providing a means for replacing the mirrors if the mirrors are broken.

After tips 104 are coupled, neck 114 is ground or otherwise polished to provide a smooth, tapering transition between body 102 and tips 104 and the geometry of the tips 104 is finished. Interface 108 may also be welded, thereby partially or totally eliminating any gap between tips 104 and body 102. Gripping surfaces 106 are surface textured, such as through sand-blasting, and a final polish may be placed on the neck 114. In one embodiment, in which steel is employed in the body 102 and/or tips 104, at some point after forming body 102 into its final shape, and forming tips 104 into their final shape, the steel body 102 and tips 104 are hardened, such as through tempering.

The sand-blasting, for example, may occur with a grit having a size in the range of about 30 microns to about 500 microns. A preferred grit size ranges from about 50 microns to about 150 microns.

It will also be appreciated that it is possible to randomly texture a portion of tip 104 to assist a practitioner in gripping tool 100. One skilled in the art will appreciate that tool 100 thus comprises a gripping portion having a randomly textured gripping surface, the gripping portion disposed between opposing ends, at least one of the ends being configured for use in a dental or medical procedure. In one embodiment, the gripping portion comprises body 102. In another embodiment, the gripping portion comprises body 102 and a portion of a tip 104 which is configured to be held by a practitioner. The tip may be integral with body 102 or coupled to body 102.

Thus, in one embodiment, the end which is configured for use in a dental or medical procedure comprises the entire tip 104. In another embodiment, the end which is configured for use in such a procedure comprises only that portion of tip 104 which is not held by the practitioner during the procedure, such as a mirror or the apex of tip 104 configured for packing, excavating, cutting, or otherwise manipulating an object or a surface.

The exterior surface of body 102 and/or tip 104 may thus be randomly textured, such as by being chemically etched or electrically treated to form gripping surfaces along a portion or all of the exterior surface thereof. It will also be appreciated that the gritblasting, such as the sand-blasting performed in one embodiment may be performed along a portion or all of the exterior surface of body 102 and/or tip 104.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A tool configured to be hand-held by a practitioner, comprising:

opposing ends, at least one end being configured for use in a dental or medical procedure; and a gripping portion configured to be hand-held by a practitioner, the gripping portion disposed between the opposing ends, the gripping portion comprising means for providing a randomly textured gripping surface that is sufficiently textured to minimize slippage during use, but which also tends to minimize retention of microorganisms.

2. A hand-held tool as in claim 1, wherein the randomly textured gripping surface comprises a gritblasted gripping surface.

3. A hand-held tool as in claim 1, wherein the gripping portion comprises a body.

4. A hand held tool as in claim 3, wherein the at least one end configured for use in a dental or medical procedure comprises a tip.

5. A hand-held tool as in claim 1, wherein the texture of the gripping surface is configured such that microorganisms are not present on the gripping surface in a concentration that is substantially greater than the concentration of microorganisms on a non-textured portion of the gripping portion after the tool has been used in a dental or medical procedure and is subsequently cleaned.

6. A hand-held tool as in claim 1, wherein the randomly textured gripping surface includes peaks and valleys which are densely and irregularly dispersed on the body.

7. A hand-held tool as in claim 1, wherein the randomly textured gripping surface includes peaks and valleys, and wherein the peaks and valleys vary in size and shape.

8. A tool configured to be hand-held by a practitioner, comprising:

a gripping portion configured to be hand-held by a practitioner, the gripping portion having a randomly textured gripping surface, wherein the gripping surface is sufficiently textured to prevent a practitioners fingers from slipping during use of the tool, while also providing minimal microbial contaminant retention; and a tip extending from the body.

9. A hand-held tool as in claim 8, wherein the randomly textured gripping surface comprises a sandblasted gripping surface.

10. A hand-held tool as in claim 8, wherein the randomly textured gripping surface comprises a chemically-etched gripping surface.

11. A hand-held tool as in claim 8, wherein the texture of the gripping surface is configured such that microorganisms are not present on the gripping surface in a concentration that is substantially greater than the concentration of microorganisms on a non-textured portion of the body after the tool has been used in a dental or medical procedure and is subsequently cleaned.

12. A hand-held tool as in claim 8, wherein the randomly textured gripping surface includes peaks and valleys which are densely and irregularly dispersed on the body.

13. A hand-held tool as in claim 8, wherein the randomly textured gripping surface includes peaks and valleys, and wherein the peaks and valleys vary in size and shape.

* * * * *

UNITED STATES PATENT AND TRADEMARK OFFICE
CERTIFICATE OF CORRECTION

PATENT NO. : 6,042,378　　　　　　　　　　　　　　　　　　　　Page 1 of 1
DATED : March 28, 2000
INVENTOR(S) : Dan E. Fischer; Dan J. Bills It is certified that error appears in the above-identified patent and that said Letters Patent is hereby corrected as shown below:

Column 3,
Line 10, change "handheld" to --hand-held--.

Column 10,
Line 42, change "practitoners" to --practitoner's--

Column 10,
Line 59, after "the" change "randonly" to --randomly--

Signed and Sealed this

Third Day of July, 2001

*Attest:*

*Attesting Officer*　　　　　NICHOLAS P. GODICI
　　　　　　　　　　　　*Acting Director of the United States Patent and Trademark Office*